(12) United States Patent
Witinski et al.

(10) Patent No.: US 9,140,606 B2
(45) Date of Patent: Sep. 22, 2015

(54) HETERODYNE OFF-AXIS INTEGRATED CAVITY OUTPUT SPECTROSCOPY

(75) Inventors: Mark Francis Witinski, Cambridge, MA (US); Pietro Malara, Cambridge, MA (US); Gianluca Gagliardi, Naples (IT)

(73) Assignees: President and Fellows of Harvard College, Cambridge, MA (US); Consiglio Nazionale Delle Ricerche, Rome (IT)

( * ) Notice: Subject to any disclaimer, the term of this patent is extended or adjusted under 35 U.S.C. 154(b) by 469 days.

(21) Appl. No.: 13/450,844

(22) Filed: Apr. 19, 2012

(65) Prior Publication Data

US 2012/0300209 A1  Nov. 29, 2012

Related U.S. Application Data

(60) Provisional application No. 61/476,772, filed on Apr. 19, 2011.

(51) Int. Cl.

| | |
|---|---|
| *G01N 21/00* | (2006.01) |
| *G01N 21/25* | (2006.01) |
| *G01J 3/433* | (2006.01) |
| *G01N 21/3504* | (2014.01) |

(Continued)

(52) U.S. Cl.
CPC ............. *G01J 3/433* (2013.01); *G01N 21/3504* (2013.01); *G01N 21/39* (2013.01); *G01N 21/031* (2013.01); *G01N 21/359* (2013.01); *G01N 2021/399* (2013.01); *G01N 2201/067* (2013.01); *G01N 2201/0691* (2013.01)

(58) Field of Classification Search
CPC ........... G01J 3/433; G01J 3/4338; G01J 3/42; G01N 2201/0691; G01N 29/42; G01N 21/39; G01N 21/3504; G01N 21/1702

USPC .................................................. 356/432, 409
See application file for complete search history.

(56) References Cited

U.S. PATENT DOCUMENTS 6,618,148 B1 *  9/2003  Pilgrim et al. ................. 356/432
6,795,190 B1     9/2004  Paul et al.
(Continued)

OTHER PUBLICATIONS

R.M. Mihalcea, M.E. Webber, D.S. Baer, R.K. Hanson, G.S. Feller, W.B. Chapman, "Diode-laser absorption measurements of CO2, H2O, N2O, and NH3 near 2.0 µm," Appl. Phys. B 67, 283-288 (1998).

(Continued)

*Primary Examiner* — Tarifur Chowdhury
*Assistant Examiner* — Sunghee Y Gray
(74) *Attorney, Agent, or Firm* — 24IP Law Group; Timothy R DeWitt

(57) ABSTRACT

An absorption spectroscopy instrument with a light source for providing a beam of light, a modulator to produce a modulated beam of light, a high finesse optical cavity, means for injecting the modulated beam of light off-axis into the high finesse optical cavity and a detector positioned to receive and measure light exiting through said optical cavity. The detector may be a highly sensitive and high bandwidth detector. The modulator may be a one or two-tone modulator having means, such as a plurality of RF synthesizers, for modulating the light source by one or two tones. If one tone of applied modulation is used, the frequency is larger than the absorption bandwidth of the target chemical. In the case where two tones are used, the first frequency is larger than the absorption bandwidth of the target chemical and the second frequency is small relative to the first frequency.

17 Claims, 5 Drawing Sheets

(51) Int. Cl.
*G01N 21/39* (2006.01)
*G01N 21/03* (2006.01)
*G01N 21/359* (2014.01)

(56) References Cited

U.S. PATENT DOCUMENTS

| | | | | |
|---|---|---|---|---|
| 7,379,652 | B2 * | 5/2008 | Cole et al. | 385/147 |
| 8,330,956 | B1 * | 12/2012 | Seletskiy et al. | 356/432 |
| 2007/0246653 | A1 * | 10/2007 | Zhou | 250/339.1 |
| 2008/0179530 | A1 * | 7/2008 | Liu et al. | 250/343 |

OTHER PUBLICATIONS

E.C. Richard, K.K. Kelly, R.H. Winkler, R. Wilson, T.L. Thompson, R.J. Mclaughlin, A.L. Schmeltekopf, A.F. Tuck, "A fast-response near-infrared tunable diode laser absorption spectrometer for in situ measurements of CH4 in the upper troposphere and lower stratosphere," Appl. Phys. B 75, 183-194 (2002).
G. Gagliardi, R. Restieri, G. De Biasio, P. De Natale, F. Cotrufo, and L. Gianfrani, "Quantitative diode laser absorption spectroscopy near 2 μm with high precision measurements of CO2 concentration," Rev. Sci. Instrum. 72, 4228-4233 (2001).
H. Dahnke, D. Kleine, W. Urban, P. Hering, M. Mürtz, "Isotopic ratio measurement of methane in ambient air using mid-infrared cavity leak-out spectroscopy," Appl. Phys. B 72, 121-125 (2001).
L. Menzel, A.A. Kosterev, R.F. Curl, F.K. Tittel, C. Gmachl, F. Capasso, D.L. Sivco, J.N. Baillargeon, A.L. Hutchinson, A.Y. Cho, W. Urban, "Spectroscopic detection of biological NO with a quantum cascade laser," Appl. Phys. B 72, 1-5 (2001).
H. Dahnke, D. Kleine, P. Hering, M. Mürtz, "Real-time monitoring of ethane in human breath using mid-infrared cavity leak-out spectroscopy," Appl. Phys. B 72, 971-975 (2001).
G.J. German, and D.J. Rokestraw, "Multiplex spectroscopy: determining the transition moments and absolute concentrations of molecular species," Science 264, 1750-1753 (1994).
C.R. Webster, "measuring methane and its isotopes 12CH4, 13CH4 and CH3D on the surface of Mars with in situ laser spectroscopy," Appl. Opt. 44, 1226-1234 (2005).
D. Romanini, A. A. Kachanov, N. Sadeghi, and F. Stockel, "CW cavity ring down spectroscopy," Chem.Phys. Lett. 264, 316-322 (1997).
K. Nakagawa, T. Katsuda, A. S. Shelkovnikov, M. de Labachelerie, and M. Ohtsu, "Highly sensitive detection of molecular absorption using a high finesse optical cavity," Opt. Commun. 107, 369-372 (1994).
J.M. Supplee, E.A. Whittaker, W. Lenth, "Theoretical description of frequency modulation and wavelength modulation spectroscopy," Appl. Opt. 33, 6294 (1994).
G.C. Bjorklund, "Frequency-Modulation Spectroscopy: A New Method for Measuring Weak Absorptions and Dispersions," Opt. Lett. 5, 15 (1980).
P. Werle, F. Slemr, M. Gehrtz, and C. Bräuchle, "Quantum-Limited FM-Spectroscopy with a Lead-Salt Diode Laser," Appl. Phys. B 49, 99-108 (1989).
J.A. Silver, "Frequency-modulation spectroscopy for trace species detection: theory and comparison among experimental methods," Appl. Opt. 31, 707-717 (1992).
J. Ye, Long-Sheng Ma, and J.L. Hall, "Ultrasensitive detections in atomic and molecular physics: demonstration in molecular overtone spectroscopy" J. Opt. Soc. Am B 15, 6-15 (1998).
D.R. Herriott, H. Kogelnik, and R. Kompfner, "Off-Axis Paths in Spherical Mirror Interferometers," Appl. Opt. 3, 523-526 (1964).
J. B. Paul, L. Lapson, and J. Anderson, "Ultrasensitive absorption spectroscopy with a high-finesse optical cavity and off-axis alignment," Appl. Opt. 40, 4904-4910 (2001).
V.L. Kasyutich, C.E. Canosa-Mas, C. Pfrang, S. Vaughan, and R.P. Wayne, "Off-axis continuous-wave cavity-enhanced absorption spectroscopy of narrow-band and broadband absorbers using red diode lasers" Appl. Phys. B 75, 755-761(2002).
Y. A. Bakhirkin, A. A. Kosterev, C. Roller, R. F. Curl, and F. K. Tittel, "Wavelength modulation off-axis integrated cavity output spectroscopy for biogenic NO detection in human breath," in Conference on Lasers and Electro-Optics/International Quantum Electronics Conference and Photonic Applications Systems Technologies, Technical Digest (CD) (Optical Society of America, 2004), paper CThT71.
Zhao, W.; Gao, X; Chen, W.; Zhang, W.; Huang, T.; Wu, T.; Cha, H. "Wavelength modulated off-axis integrated cavity output spectroscopy in the near infrared" App. Phys. B. vol. 86, N. 2, 2007 , pp. 353-359.
M. F. Witinski, D. S. Sayres, and J. G. Anderson, "High Precison Methane Isotopolog Measurements at Ambient Mixing Ratios Using Integrated Cavity Output Sepctroscopy," Appl. Phys. B. DOI: 10.1007/s00340-010-3957-2.
D.E. Cooper, J.P. Watjen, "Two-tone optical heterodyne spectroscopy with a tunable lead-salt diode laser," Opt. Lett. 11, 606 (1986).
P. Werle: Spectrochimica Acta Part A: Molecular and Biomolecular Spectroscopy, vol. 54, issue 2, pp. 197-236.

* cited by examiner

HETERODYNE OFF-AXIS INTEGRATED CAVITY OUTPUT SPECTROSCOPY

CROSS-REFERENCE TO RELATED APPLICATIONS

The present application claims the benefit of the filing date of U.S. Provisional Patent Application Ser. No. 61/476,772 filed by the present inventors on Apr. 19, 2011, entitled "Heterodyne Off-Axis Integrated Cavity Output Spectroscopy For Detection Of Trace Atmospheric Species And Their Isotopologues," which is hereby incorporated by reference herein in its entirety.

STATEMENT REGARDING FEDERALLY SPONSORED RESEARCH OR DEVELOPMENT

None.

BACKGROUND OF THE INVENTION

1. Field of the Invention

The present invention relates to high sensitivity spectroscopy.

2. Brief Description of the Related Art

Sensitivity of spectroscopic detection is a crucial issue for applications where trace gas chemicals are to be measured. Atmospheric chemistry, environmental monitoring, biomedical diagnostics and molecular astrophysics are just a few examples of areas of research demanding for ultra-sensitive and rugged setups, capable of field measurements. See, for example, R. M. Mihalcea, M. E. Webber, D. S. Baer, R. K. Hanson, G. S. Feller, W. B. Chapman, "*Diode-laser absorption measurements of $CO_2$, $H_2O$, $N_2O$, and $NH_3$ near $2.0\,\mu m$,*" Appl. Phys. B 67, 283-288 (1998); E. C. Richard, K. K. Kelly, R. H. Winkler, R. Wilson, T. L. Thompson, R. J. Mclaughlin, A. L. Schmeltekopf, A. F. Tuck, "*A fast-response near-infrared tunable diode laser absorption spectrometer for in situ measurements of $CH_4$ in the upper troposphere and lower stratosphere,*" Appl. Phys. B 75, 183-194 (2002); G. Gagliardi, R. Restieri, G. De Biasio, P. De Natale, F. Cotrufo, and L. Gianfrani, "*Quantitative diode laser absorption spectroscopy near $2\,\mu m$ with high precision measurements of $CO_2$ concentration,*" Rev. Sci. Instrum. 72, 4228-4233 (2001); H. Dahnke, D. Kleine, W. Urban, P. Hering, M. Mürtz, "*Isotopic ratio measurement of methane in ambient air using mid-infrared cavity leak-out spectroscopy,*" Appl. Phys. B 72, 121-125 (2001); L. Menzel, A. A. Kosterev, R. F. Curl, F. K. Tittel, C. Gmachl, F. Capasso, D. L. Sivco, J. N. Baillargeon, A. L. Hutchinson, A. Y. Cho, W. Urban, "*Spectroscopic detection of biological NO with a quantum cascade laser,*" Appl. Phys. B 72, 1-5 (2001); H. Dahnke, D. Kleine, P. Hering, M. Mürtz, "*Real-time monitoring of ethane in human breath using mid-infrared cavity leak-out spectroscopy,*" Appl. Phys. B 72, 971-975 (2001); and G. J. German, and D. J. Rokestraw, "*Multiplex spectroscopy: determining the transition moments and absolute concentrations of molecular species,*" Science 264, 1750-1753 (1994); C. R. Webster, "*measuring methane and its isotopes $^{12}CH_4$, $^{13}CH_4$ and $CH_3D$ on the surface of Mars with in situ laser spectroscopy,*" Appl. Opt. 44, 1226-1234 (2005).

In general, for most of spectroscopic methods, the Beer-Lambert law that underpins much of molecular absorption spectroscopy leaves two clear paths to improve the detection sensitivity: increasing the radiation/sample interaction pathlength and reducing the noise that affects the absorption signal.

With regard to the first, there are a number of well-established methods for absorption length enhancement, the most effective of which exploit the several-kilometers paths attainable in high finesse optical cavities. Techniques such as cavity ring-down spectroscopy (CRDS), cavity-enhanced absorption spectroscopy (CEAS) and integrated cavity output spectroscopy (ICOS), demonstrated minimum detectable absorption coefficients ranging from $10^{-8}\,cm^{-1}\,Hz^{-1/2}$ to $10^{-11}\,cm^{-1}\,Hz^{-1/2}$. See, D. Romanini, A. A. Kachanov, N. Sadeghi, and F. Stockel, "*CW cavity ring down spectroscopy,*" Chem. Phys. Lett. 264, 316-322 (1997) and K. Nakagawa, T. Katsuda, A. S. Shelkovnikov, M. de Labachelerie, and M. Ohtsu, "*Highly sensitive detection of molecular absorption using a high finesse optical cavity,*" Opt. Commun. 107, 369-372 (1994).

As for noise suppression, different strategies are usually adopted for the various optical and electronic noise components. For example, high speed ensemble averaging can reduce white noise of a detector and its associated electronics while antireflection coatings can suppress the optical noise that often limits the sensitivity of laser-based spectrometers.

Since the 1980's heterodyne detection schemes have been employed to suppress the technical 1/f (flicker) noise associated with all laser sources and most photodetectors. See, J. M Supplee, E. A. Whittaker, W. Lenth, Appl. Opt. 33, 6294 (1994); D. E. Cooper, J. P. Watjen, Opt. Lett. 11, 606 (1986); and G. C. Bjorklund, Opt. Lett. 5, 15 (1980). The general principle underlying these methods consists of modulating the laser current to produce a pair of sidebands on the laser carrier and, after interaction with the sample, detecting and demodulating their beat frequency by means of phase-sensitive electronics. In this way, a sample's absorption depth and linewidth are encoded at the modulation frequency, which can be set in the radiofrequency (RF) domain, where the flicker noise is reduced by a few orders of magnitude. Many variations of this basic heterodyne detection scheme have been successfully applied, providing in some cases sensitivity enhancements up to two orders of magnitude with respect to traditional laser spectroscopy. See, P. Werle, F. Slemr, M. Gehrtz, and C. Bräuchle: Appl. Phys. B 49, 99 (1989); J. A. Silver: Appl. Opt. 31, 707 (1992); and P. Werle: Spectrochim. Acta Part A 54, 197 (1998).

Additionally, in U.S. Pat. No. 6,795,190, a method and apparatus was disclosed in which a continuous wave light beam was introduced into a cavity using off-axis cavity alignment to systematically eliminate optical resonant noise commonly associated with optical cavities while preserving the absorption signal amplifying properties of such cavities.

The realization of a technique that combines the signal enhancement of cavity-based techniques with the noise suppression of a heterodyne detection scheme has proven nontrivial. It was addressed only in 1998 by Ye et al., with a technique called noise-immune cavity-enhanced optical-heterodyne molecular spectroscopy (NICE-OHMS). See, J. Ye, Long-Sheng Ma, and J. L. Hall, "*Ultrasensitive detections in atomic and molecular physics: demonstration in molecular overtone spectroscopy*" J. Opt. Soc. Am B 15, 6-15 (1998). In NICE-OHMS, the radiation injected in the optical resonator is modulated at a frequency that is a multiple of the cavity mode spacing (FSR), thus creating a couple of sidebands available at the cavity output. Then, the transmitted signal is heterodyned to retrieve information on the intracavity absorption. In this way, an unprecedented shot-noise limited detection sensitivity, as low as $10^{-14}\,cm^{-1}\,Hz^{-1/2}$ was demonstrated in the near infrared. However, in order to be transmitted by the cavity, both carrier and modulation sidebands must be constantly in resonance with three cavity modes. To achieve this condition, the cavity mode spacing or free spectral range (FSR) and the laser frequency need to be stabilized independently by means of tight, fast, and low-noise frequency-locking schemes. As a consequence, the setup is technically extremely demanding and particularly sensitive to mechanical shocks and vibrations. This makes the extraordinary high sensitivity reachable by NICE-OHMS only attainable in laboratory environments.

SUMMARY OF THE INVENTION

The present invention is a new spectroscopic detection scheme, based on an off-axis injection of a high finesse cavity in combination with a single or two-tone high-frequency modulation technique. This new method and apparatus, which may be referred to as FM-ICOS (and its variation TTFM-ICOS presented below), requires no active control of the cavity length and is relatively straightforward to implement electronically, allowing for facile conversion of existing ICOS setups to perform FM-ICOS while still maintaining the ability to carry out traditional ICOS, simply by turning off the modulation. The present invention is not limited to a specific spectral region and/or laser source. This technique works equally for any laser source whose frequency can be modulated by an electronic or electro-optic device at a rate of greater than hundreds of kHz. In a preferred embodiment, the present invention is an absorption spectroscopy instrument. The instrument is comprised of a coherent light source such as a laser for providing a beam of light, a modulator or means to produce a frequency modulated beam of light, a high finesse optical cavity having a pair of mirrors defining an axial light path in the optical cavity, means (such as a mirror or mirrors) for injecting the modulated beam of light off-axis into the high finesse optical cavity, a detector positioned to receive and measure light exiting through the optical cavity and means to demodulate the detector signal, or to extract from it the Fourier component at the modulation frequency (or at one of its harmonics). The modulator or means for modulating may be a one or a two-tone modulator having means for modulating the light source by one or two different tones. In the case where two modulation frequencies are used, the first frequency is larger than the absorption linewidth of the target chemical and the second frequency is small relative to the first frequency. The demodulator may be a fast lock-in amplifier as well as a frequency mixer.

In a preferred embodiment, the present invention is an absorption spectroscopy instrument. The instrument comprises a light source for providing a beam of light, a means for modulating the beam of light using at least one frequency that is greater than 100 kHz to produce a modulated beam of light, a high finesse optical cavity comprising a pair of mirrors defining an axial light path in the high finesse optical cavity, means for injecting the modulated beam of light off-axis into the high finesse optical cavity, a detector positioned to detect light exiting through the high finesse optical cavity, and means for demodulating light detected by the detector and extracting a component that is modulated at one of an applied modulation frequency or a harmonic of an applied modulation frequency. The detector may comprise, for example, a highly sensitive high bandwidth detector. The means for modulating the beam of light may comprise means for modulating the beam of light by one tone where the modulation the frequency is larger than the absorption bandwidth of a target chemical. The means for modulating the beam of light alternatively may comprises means for modulating the beam of light by two tones where a first frequency is larger than the absorption bandwidth of the target chemical and a second frequency is small relative to the first frequency. The means for modulating the light source may comprise, for example, an RF synthesizer, an acousto-optic modulator, an electro-optic modulator, a second light source, a plurality of any of those or a combination of those.

In another preferred embodiment, the absorption spectroscopy instrument comprises a light source for providing a beam of light, a modulator, wherein the modulator modulates the light source using at least one frequency that is greater than 100 kHz to produce a modulated beam of light, a high finesse optical cavity having an axial light path, means for injecting the modulated beam of light off-axis into the high finesse optical cavity, a detector positioned to receive and measure light exiting through the high finesse optical cavity, and a demodulator, wherein the demodulator demodulates a signal received from the detector and extracts a component that is modulated at one of an applied modulation frequency or a harmonic of an applied modulation frequency. The means for injecting may comprise, for example, a mirror or mirrors.

In yet another embodiment, the present invention is a method for performing absorption spectroscopy. The method comprises the steps of providing a beam of light, modulating the beam of light using at least one frequency that is greater than 100 kHz to produce a modulated beam of light, injecting the modulated beam of light off-axis into a high finesse optical cavity; and demodulating light exiting through the high finesse optical cavity and extracting a component of the light exiting from the high finesse cavity that is modulated at one of an applied modulation frequency or a harmonic of an applied modulation frequency. The step of modulating the beam of light may comprises modulating the beam of light by one tone where the modulation the frequency is larger than the absorption bandwidth of a target chemical. Alternatively, the step of modulating the beam of light may comprise modulating the beam of light by two tones where a first frequency is larger than the absorption bandwidth of the target chemical and a second frequency is small relative to the first frequency.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1A:
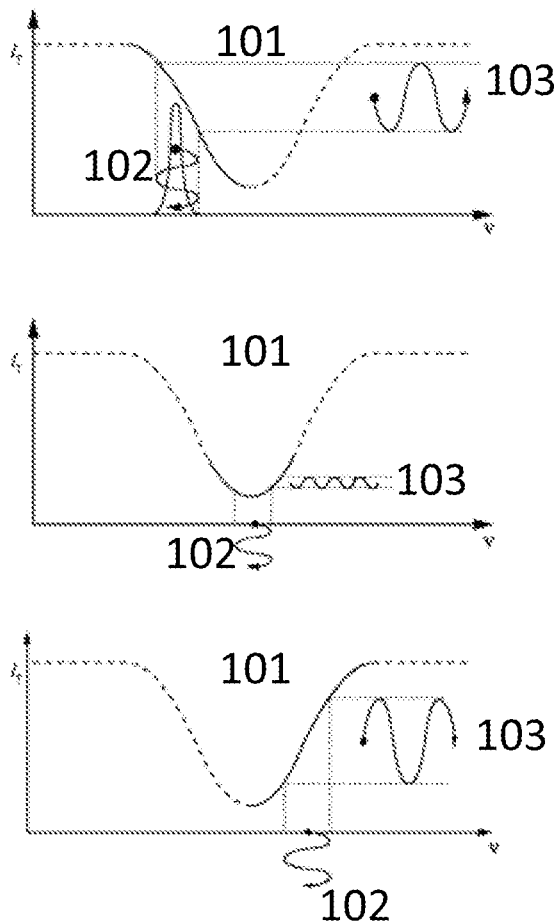
FIGS. 1A and 1B illustrate a conceptual difference between harmonic and FM detection. In the harmonic detection (FIG. 1A) the absorption line converts the FM modulation in an amplitude modulated (AM) signal, depending on the absorption line's slope in every point. In FM detection (FIG. 1B) the modulation is much faster, such that the signal is produced by the differential attenuation of the modulation sidebands that resulted from the applied modulation.

The present invention provides a new detection scheme based on an off-axis injection of a high finesse cavity in combination with a frequency modulation technique.

This method, referred to as FM-ICOS or TTFM-ICOS, requires no active control of the cavity length and is relatively straightforward to implement electronically, allowing for facile conversion of existing ICOS setups to perform FM-ICOS and/or TTFM-ICOS while still maintaining the ability to carry out traditional ICOS, simply by turning off the modulation. The present invention is not limited to the mid-infrared and/or the use of a quantum cascade laser as a light source. This novel technique works equally well for example with a single mode diode laser emitting in the near infrared.

In a preferred embodiment of the invention, the off-axis laser injection geometry is analogous to that observed in Herriott multipass cell, where the multiple ray reflections between two concave mirrors trace out a series of reflections in an elliptical pattern, with a per-pass angular displacement given by $\cos\theta=1-L/r$, where L and r are, respectively, the mirror distance and curvature. See, D. R. Herriott, H. Kogelnik, and R. Kompiher, Appl. Opt. 3, 523 (1964). The ray pattern becomes re-entrant when $2m\theta=2p\pi$, where m equals the number of optical round-trip passes and p is an integer. In this way the cavity effective free-spectral-range (FSR) equals c/2 mL. With a proper choice of L and r, the number m can be made extremely large, so that the entire cavity mode structure collapses in a continuum and the cavity effectively behaves like a non-resonant optical element.

The use of off axis injection into an optical cavity, rather than a Herriott cell, was proposed by J. B. Paul, L. Lapson, and J. Anderson, "*Ultrasensitive absorption spectroscopy with a high-finesse optical cavity and off-axis alignment*," Appl. Opt. 40, 4904-4910 (2001). In this technique, called off-axis integrated cavity output spectroscopy (ICOS), time integration of the output signal is used to average out the residual mode structure of the off axis cavity. Additional laser-frequency and cavity-length dithering can be introduced to help in achieving the non-resonant condition, where the cavity behaves effectively like a single-pass absorption cell of length LF/$\pi$, where F is the finesse.

In practice, the actual sensitivity enhancement of the ICOS method compared to traditional multipass spectroscopy relies on the ability to smooth out the cavity resonance structure. While in traditional multipass cells mechanical vibrations can create unstable patterns of interferences that are difficult to average out, in ICOS the mechanical vibrations as well as the small misalignments which are usually unwanted, contribute to the scrambling of the mode structure and therefore to the suppression of the excess cavity resonant noise. The technique is inherently robust and fieldable.

The FM-ICOS method in accordance with the present invention comprises exploiting the quasi-continuum of ICOS cavity transmission to perform a cavity-enhanced heterodyne detection without need for any frequency locking loop or active stabilization. In fact, having no resonance condition to be met, the off-axis alignment guarantees in principle that any laser carrier with its modulation sidebands is transmitted by the cavity, allowing the beat note between sidebands to be detected, demodulated, and recorded as an absorption signal. Such a detection scheme can therefore benefit both of the cavity signal enhancement and the heterodyne technical noise reduction, while preserving the ruggedness typical of OA-ICOS.

A few examples of OA-ICOS associated with modulation and lock-in harmonic detection exist in literature. These experiments were performed only in the low modulation frequency regime, but still demonstrated, in a fully optimized setup, up to one order of magnitude sensitivity improvement with respect to traditional ICOS. See, V. L. Kasyutich, C. E. Canosa-Mas, C. Pfrang, S. Vaughan, and R. P. Wayne, "*Off-axis continuous-wave cavity-enhanced absorption spectroscopy of narrow-band and broadband absorbers using red diode lasers*" Appl. Phys. B 75, 755-761 (2002); Y. A. Bakhirkin, A. A. Kosterev, C. Roller, R. F. Curl, and F. K. Tittel, "*Wavelength modulation off-axis integrated cavity output spectroscopy for biogenic NO detection in human breath*," in Conference on Lasers and Electro-Optics/International Quantum Electronics Conference and Photonic Applications Systems Technologies, Technical Digest (CD) (Optical Society of America, 2004), paper CThT71; and Zhao, W.; Gao, X; Chen, W.; Zhang, W.; Huang, T.; Wu, T.; Cha, H. "*Wavelength modulated off-axis integrated cavity output spectroscopy in the near infrared*" App. Phys. B. Vol. 86, N.2, 2007, pp. 353-359.

Although also based on a modulation/demodulation scheme, the above mentioned techniques are radically different from the proposed FM scheme. In WMS, a very slow modulation ($f_m$<<than the investigated absorption line width $\gamma$) is used. Therefore the detection relies on the principle of harmonic detection: where frequency-to-amplitude modulation conversion is effected by the absorption line. In this sense, WMS can be regarded as a standard harmonic lock-in technique, improved by a larger modulation amplitude (see FIG. 1A). In the harmonic detection the absorption line 101 converts the modulation 102 into an amplitude modulated (AM) signal 103, depending on the absorption line's slope in every point. The three panels of FIG. 1A illustrate this conversion for three different center wavelengths as the center wavelength is tuned relative to the absorption line.

Figure 1B:
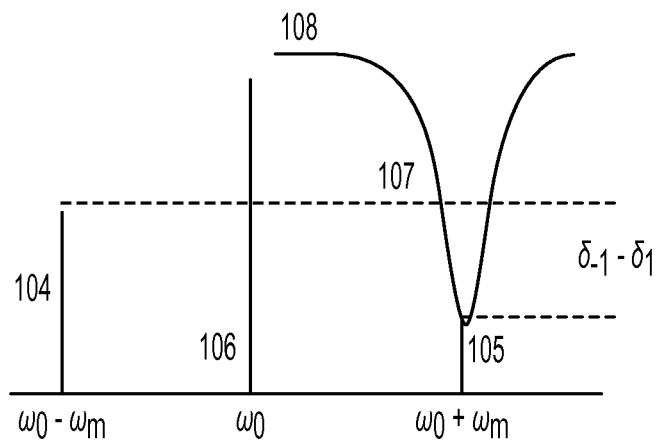

In FM spectroscopy, the modulation frequency is much larger than the width of the absorption line under investigation, as shown in FIG. 1B. Such a difference leads to a conceptually different type of detection. Two well distinguished, phase locked sidebands 104 and 105 are created, and propagate in the cavity with the carrier 106 as independent sources at frequencies $f_{las}\pm f_m$. The beat note created at frequency $2f_m$, represents the heterodyne signal to be detected and then detected and brought back to baseband. In fact, since the sidebands have equal amplitudes and opposite phases, their beat note cancels out completely unless one of them is partially absorbed. The condition on the frequency ($f_m$>>$\gamma$) ensures that only one sideband per time interacts with the sample (see FIG. 1B). so that the instantaneously, the difference between absorption line 107 and baseline 108 is detected.

Straightforwardly, going to a higher frequency-modulation regime is expected to reduce to a much larger extent the 1/f noise. Also, the more the modulation frequency exceeds the cavity 3 dB lowpass cutoff at $½\pi\tau$ (where $\tau$ is the cavity ringdown time) the more the laser residual amplitude modulation (RAM) is attenuated at the cavity output. This can be a crucial point since RAM is one of the main noise sources in all the frequency modulation setups (in particular when using lasers with high slope efficiency, such as QCLs). Despite the mentioned advantages, a proper heterodyne technique in an off-axis cavity has not previously been demonstrated.

One critical issue in combining ICOS with an FM technique is represented by detector's performance. FM-ICOS requires a photodetector 230 that is at once highly sensitive and has an extremely high bandwidth (typically FM techniques require detector bandwidths in the hundreds of MHz). In order to still exploit the general advantages of frequency modulation despite the bandwidth limitation in the absence of such detectors, an embodiment of the present invention uses a two-tone frequency modulation spectroscopic technique (TTFM-ICOS).

In TTFM-ICOS the laser is modulated by two different tones at frequencies $\Omega$ and $\omega$, rather than a single frequency as in FM spectroscopy. The frequency $\Omega$ is larger than the absorption linewidth (several hundreds of MHz), whereas $\omega$ is relatively small (hundreds of KHz to a few MHz). Such a modulation gives rise to three couples of second-order sidebands, each couple separated by $2\omega$, and centered respectively at frequencies $\omega_0-\Omega$, $\omega_0$ and $\omega_0+\Omega$, $\omega_0$. This is illustrated in FIG. 2.

Under these conditions, the signal at the detector shows a beat component at $2\omega$ proportional to the differential attenuation of the three doublets, which carries information on the sample absorption, and can be written as $$I(t) \propto m^2 e^{-2\delta_0}[1+(2\delta_0-\delta_+\delta_-)\cos 2\omega t] \quad (1)$$

Where m is the modulation index and $\delta_0$, $\delta_+$, $\delta_-$ are the attenuations of the three doublets due to absorption. Since $2\omega$ is small compared to the absorption linewidth, each second order sideband couple (−, 0, +) can be considered as experiencing an overall attenuation $\delta_{(-,0,+)}$. As Eq. 1 shows, even if radiation is modulated at the high frequency $\Omega$, the absorption signal in TTFM-ICOS system is encoded at the small beat frequency $2\omega$, and can therefore be detected by a slow, inexpensive detector.

Figure 2:
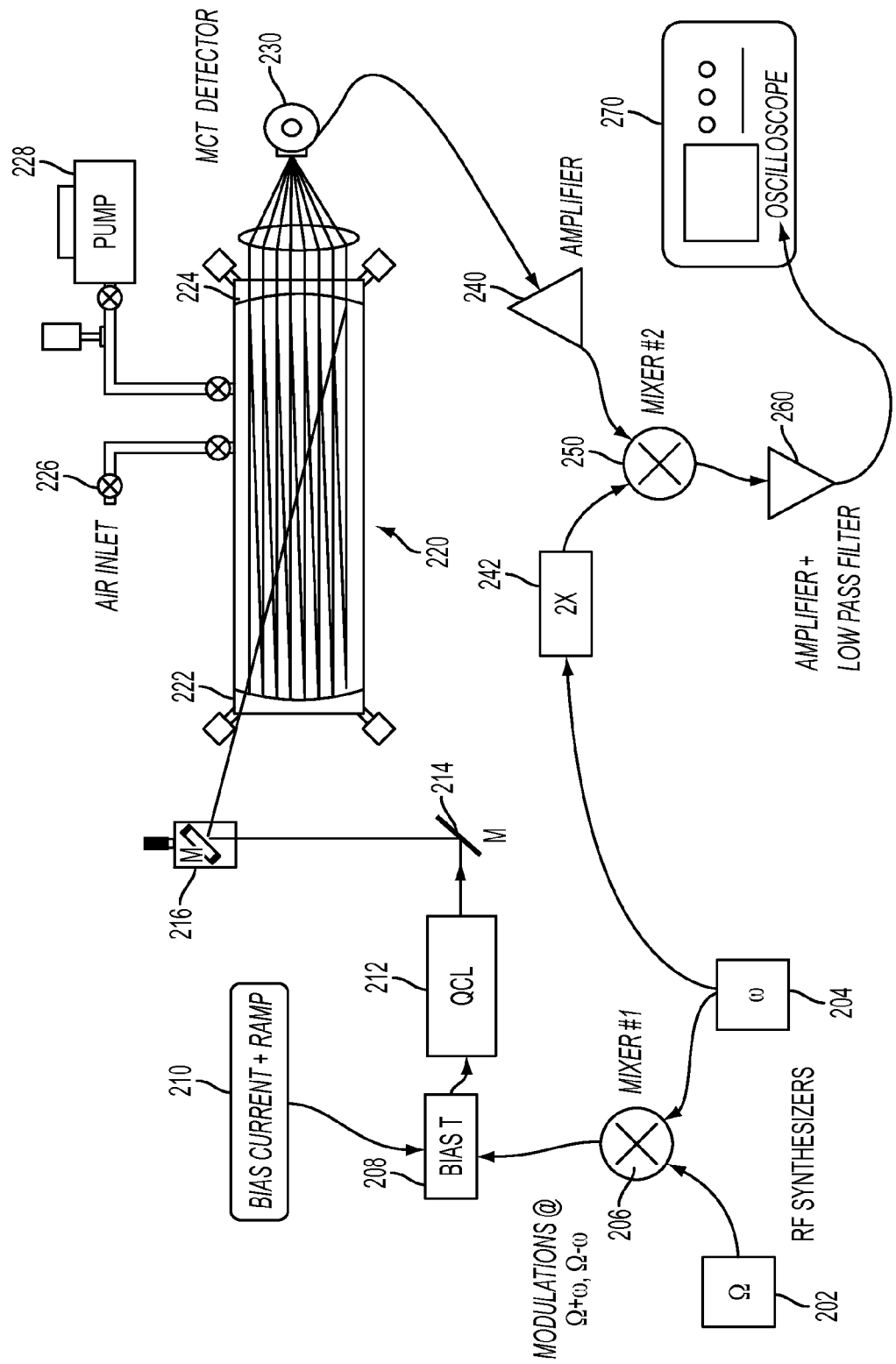
FIG. 2 is a schematic diagram of an exemplary setup used to combine off-axis integrated cavity output spectroscopy (ICOS) and Frequency Modulation, in this case two-tone frequency modulation (TTFM), in accordance with a preferred embodiment of the present invention.

As shown in FIG. 2, an exemplary setup of the present invention has two frequency synthesizers 202, 204 generate the tones $\Omega$ and $\omega$, at frequencies around 100 MHz and 10 kHz, respectively. The signals are combined by a double balanced mixer 206 to create beats at $\Omega+\omega$ and $\Omega-\omega$. Such a modulation is applied to the laser source (in this example a 1550 nm butterfly mount DFB diode) 212 by means of the AC port of a bias tee 208. On the DC port the bias current 210 is provided, along with a slower current ramp to scan across the absorption lines of interest The laser output, consisting of the carrier and its TTFM sideband structure, is then injected via mirrors 214, 216 off-axis into a 90 cm optical cavity 220 equipped with two high-reflectivity mirrors 222, 224. The cavity can be filled with by a gas analyte via inlet 226 at a controlled pressure provided by pump 228. The average mirror reflectivity, measured by ringdown decay ($\tau$=0.37 µs), is R=99.2%, yielding an equivalent absorption pathlength $L_{eff}$=LF/$\pi$=410 m. The signal is acquired by a 124 MHz bandwidth detector 230 placed behind the resonator's output mirror 224.

To retrieve the intracavity molecular absorption signal of Eq. (1), the output of detector 230 has to be amplified via amplifier 240 and sent to a second double-balanced mixer 250 along with a local oscillator (LO) signal 242 at frequency $2\omega$, split from the w frequency synthesizer 204 and doubled. The output of mixer 250 is then passed through filter 260 (lowpass 1 kHz), ensemble-averaged (128 samples) and monitored by an oscilloscope 270.

It is worth noting that, as in all the heterodyne detection schemes, the absorption signals cannot be well fit to an analytical function. The direct comparison with ICOS largely simplifies the calibration issues necessary for absolute concentration measurements. However, in case the technique is used for isotopic ratio measurements an absolute calibration is far less essential. See, M. F. Witinski, D. S. Sayres, and J. G. Anderson, "*High Precison Methane Isotopolog Measurements at Ambient Mixing Ratios Using Integrated Cavity Output Sepctroscopy*," Appl. Phys. B. DOI: 10.1007/s00340-010-3957-2.

Figure 3:
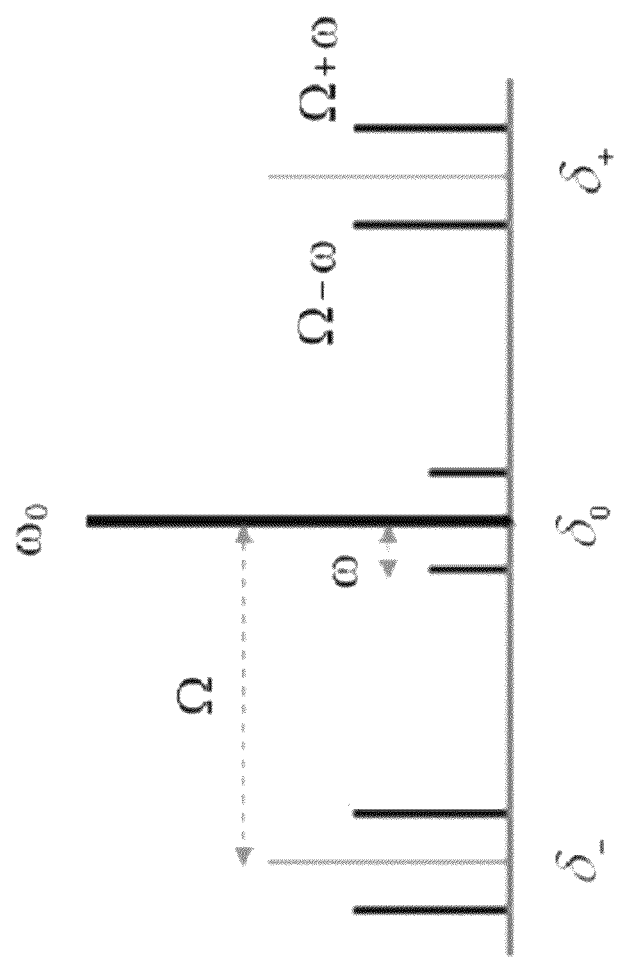
FIG. 3 is a diagram of a two-tone modulation frequency (TTFM) sideband structure with the separations of the sidebands exaggerated for purposes of illustration.
Figure 4:
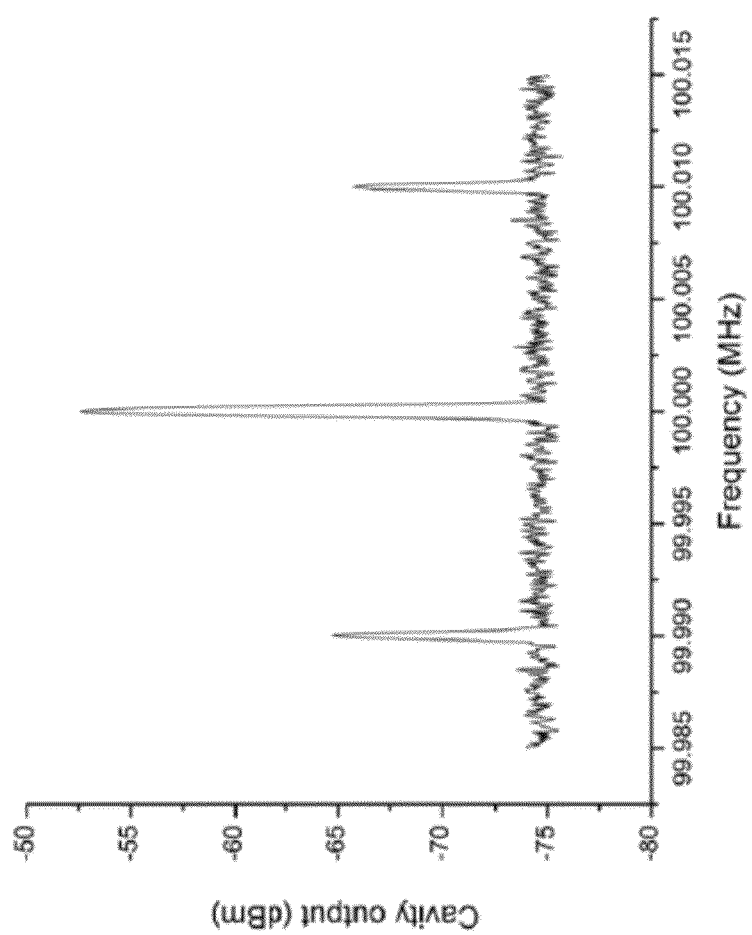
FIG. 4 presents experimental data in which the output spectrum of an optical cavity was measured with a spectrum analyzer for a TTFM experiment. The figure shows that the cavity transmits the sidebands resulting from a 1550 nm DFB laser whose current is modulated simultaneously at frequencies $\Omega=100$ MHz and $\omega=10$ kHz.

Now—what was not obvious from the prior art was that the modulation sidebands sketched in FIG. 3 would be transmitted by an optical cavity, which we have here demonstrated as shown in FIG. 4. Optical cavities are like low pass filters for light—they support certain frequencies that are resonant with the cavity while repressing others. Conventional thinking would suggest that as the laser is modulated faster and faster, the modulation would be more and more suppressed, thus reducing the ability to detect the modulation in the transmitted cavity signal. This is in fact true in the case of traditional harmonic techniques (FIG. 1A). The key to FM-ICOS is that the laser is modulated so fast such that separate frequencies (sidebands) are actually created with respect to the carrier frequency of the laser light as the modulation frequency is increased beyond the linewidth of the laser (laser linewidths of DFB diode lasers and QCLs are typically <25 MHz). To the cavity, these sidebands are less like a modulation, which may be filtered out, and more like separate laser injections at new frequencies, which are far less subject to low-pass filtering.

Another key realization is that cavity resonance structure is very complex and chaotic in the absence of active control of the cavity length. This means that tiny changes in environment that change the cavity length ever so slightly can affect its geometry and thus the frequencies that it supports. For example, even a tiny change in temperature can cause a mirror to expand ever so slightly such that the cavity becomes a different length and has therefore different resonances. The key here is that when the laser is aimed off-axis in the cavity, its effective length becomes longer and the various cavity modes "blur" together, allowing our FM or TTFM modulation to survive and transmit.

Figure 5:
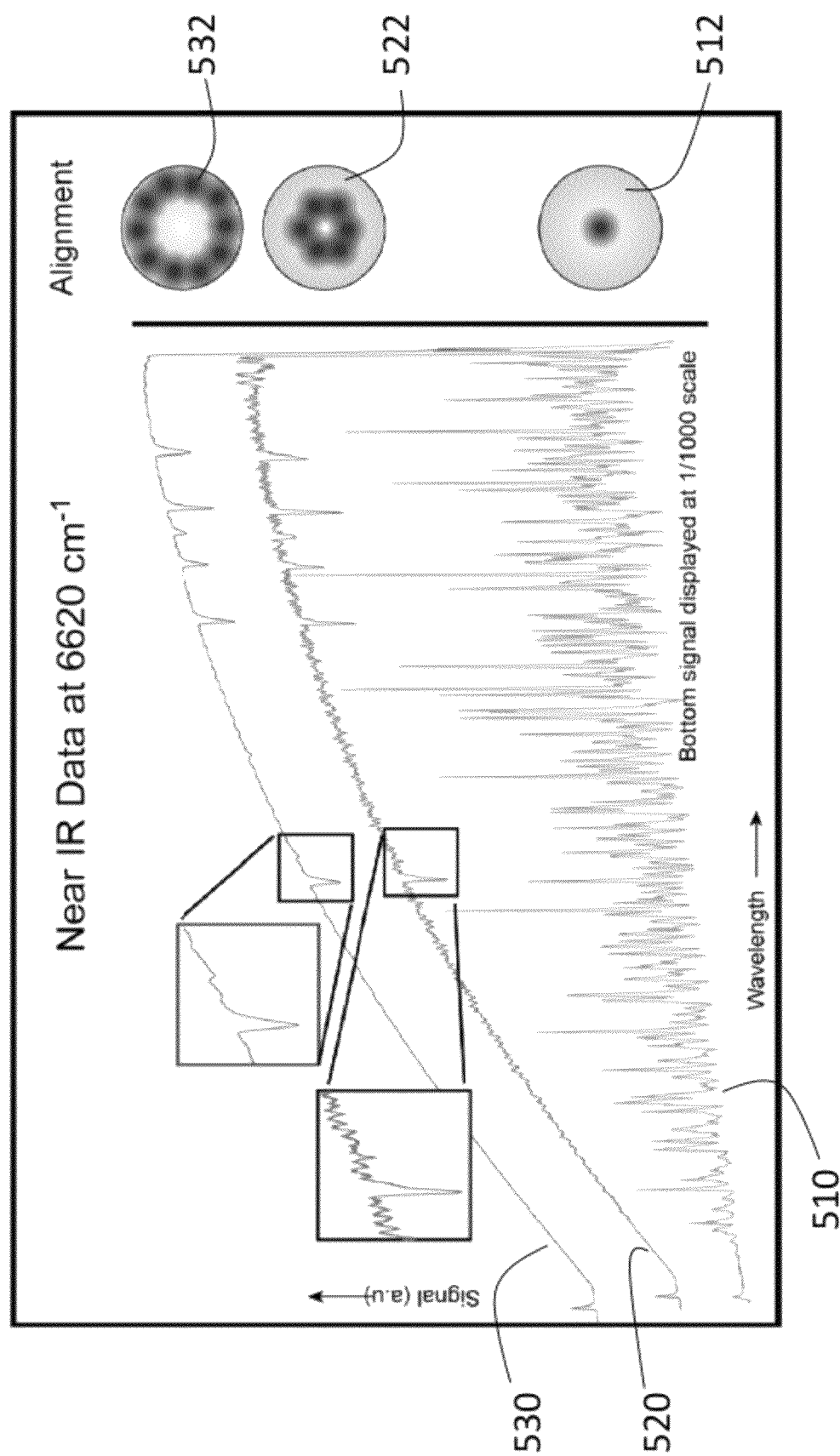
FIG. 5 is an illustration of near infrared ICOS data at 6620 cm$^{-1}$ for various injection alignments, including a visual representation of how aligning the laser more and more "off-axis" improves the signal to noise.

The ability of an off-axis cavity to smooth out cavity resonances is illustrated in FIG. 5. Looking trace 510, which correspond to aligning a cavity on axis (512), a number of messy structures exist in a cavity when a laser is aimed along the axis of the cavity. In this case one would have no hope of extracting the applied modulation. However, by following the traces up to traces 520, 530, one can see that by aligning off-axis, the spots form a circular pattern on the mirrors and the corresponding absorption spectrum does not show appreciable structure from cavity modes. They are all blurred together. Even then, it is not obvious that this enhanced smoothness from going off-axis would allow for high modulation frequencies to transmit through. However, the present invention has shown that these frequencies do in fact transmit. FIG. 4 shows experimental data from an FM-ICOS experiment where an ICOS cavity was injected with radiation from a 1550 nm DFB laser whose current is modulated simultaneously at frequencies $\Omega$=100 MHz and $\omega$=10 kHz. As shown in FIG. 4, both the center frequency at 100 MHz and both sidebands were transmitted successfully. This experiment verifies that full FM-ICOS and TTFM-ICOS spectroscopy is indeed possible.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An absorption spectroscopy instrument comprising:
   a light source for providing a beam of light;
   a means for modulating said beam of light by one tone where a modulation frequency is larger than an absorption bandwidth of a target chemical;
   a optical cavity comprising a pair of mirrors defining an axial light path in said optical cavity;
   means for injecting said modulated beam of light off-axis into said optical cavity;
   a detector positioned to detect light exiting through said optical cavity; and
   means for demodulating light detected by said detector and extracting a component that is modulated at one of an applied modulation frequency or a harmonic of an applied modulation frequency.

2. An absorption spectroscopy instrument according to claim 1 wherein said detector comprises a highly sensitive high bandwidth detector.

3. An absorption spectroscopy instrument according to claim 1 wherein said means for modulating said beam of light comprises means for modulating said beam of light by two tones where a first frequency is larger than the absorption bandwidth of the target chemical and a second frequency is small relative to the first frequency.

4. An absorption spectroscopy instrument according to claim 1 wherein said means of modulating said light source comprises at least one RF synthesizer.

5. An absorption spectroscopy instrument according to claim 1 wherein said means of modulating said light source comprises at least one acousto-optic modulator.

6. An absorption spectroscopy instrument according to claim 1 wherein said means of modulating said light source comprises at least one electro-optic modulator.

7. An absorption spectroscopy instrument according to claim 1 wherein said means of modulating said light source comprises another light source.

8. An absorption spectroscopy instrument comprising:
   a light source for providing a beam of light;
   a modulator, wherein said modulator modulates said light source by one tone where a modulation frequency is larger than an absorption bandwidth of a target chemical;
   a optical cavity having an axial light path;
   means for injecting said modulated beam of light off-axis into said optical cavity;
   a detector positioned to receive and measure light exiting through said optical cavity; and
   a demodulator, wherein said demodulator demodulates a signal received from said detector and extracts a component that is modulated at one of an applied modulation frequency or a harmonic of an applied modulation frequency.

9. An absorption spectroscopy instrument according to claim 8 wherein said means for injecting comprises a mirror.

10. An absorption spectroscopy instrument according to claim 8 wherein said modulator comprises at least one RF synthesizer.

11. An absorption spectroscopy instrument according to claim 8 wherein said modulator comprises at least one acousto-optic modulator.

12. An absorption spectroscopy instrument according to claim 8 wherein said modulator comprises at least one electro-optic modulator.

13. An absorption spectroscopy instrument according to claim 8 wherein said modulator comprises a second light source.

14. An absorption spectroscopy instrument according to claim 8 wherein said demodulator comprises a fast lock-in amplifier.

15. An absorption spectroscopy instrument according to claim 8 wherein said demodulator comprises a frequency mixer.

16. A method for performing absorption spectroscopy comprising the steps of:
    providing a beam of light;
    modulating said beam of light by one tone where a modulation frequency is larger than an absorption bandwidth of a target chemical;
    injecting said modulated beam of light off-axis into a optical cavity; and
    demodulating light exiting through said optical cavity and extracting a component of said light exiting from said cavity that is modulated at one of an applied modulation frequency or a harmonic of an applied modulation frequency.

17. A method for performing absorption spectroscopy according to claim 16, wherein said step of modulating said beam of light comprises modulating said beam of light by two tones where a first frequency is larger than the absorption bandwidth of the target chemical and a second frequency is small relative to the first frequency.

* * * * *